United States Patent
Amagasa et al.

(10) Patent No.: US 10,617,310 B2
(45) Date of Patent: Apr. 14, 2020

(54) INFORMATION PROCESSING DEVICE AND INFORMATION PROCESSING METHOD

(71) Applicant: SONY SEMICONDUCTOR SOLUTIONS CORPORATION, Kanagawa (JP)

(72) Inventors: Yuya Amagasa, Kanagawa (JP); Kazuo Kumano, Kanagawa (JP)

(73) Assignee: SONY SEMICONDUCTOR SOLUTIONS CORPORATION, Kanagawa (JP)

(*) Notice: Subject to any disclaimer, the term of this patent is extended or adjusted under 35 U.S.C. 154(b) by 68 days.

(21) Appl. No.: 15/741,010

(22) PCT Filed: Jul. 22, 2016

(86) PCT No.: PCT/JP2016/071565
§ 371 (c)(1),
(2) Date: Dec. 29, 2017

(87) PCT Pub. No.: WO2017/022525
PCT Pub. Date: Feb. 9, 2017

(65) Prior Publication Data
US 2018/0192889 A1    Jul. 12, 2018

(30) Foreign Application Priority Data

Aug. 6, 2015   (JP) .................................. 2015-156080

(51) Int. Cl.
*A61B 5/026*          (2006.01)
*H01M 8/16*           (2006.01)
(Continued)

(52) U.S. Cl.
CPC .............. *A61B 5/022* (2013.01); *A61B 5/026* (2013.01); *A61B 5/1455* (2013.01);
(Continued)

(58) Field of Classification Search
CPC ... A61B 5/022; A61B 5/14551; A61B 5/1455; A61B 5/026; H01M 8/16; H01M 2250/30; Y02E 60/527
See application file for complete search history.

(56) References Cited

U.S. PATENT DOCUMENTS

| 5,709,216 A | 1/1998 | Woodson, III |
| 5,791,345 A | 8/1998 | Ishihara et al. |

(Continued)

FOREIGN PATENT DOCUMENTS

| CA | 2676407 A1 | 8/2008 |
| CN | 101686800 A | 3/2010 |

(Continued)

OTHER PUBLICATIONS

Erickson. "Size and Shape of Protein Molecules at the Nanometer Level Determined by Sedimentation, Gel Filtration, and Electron Microscopy." Biological Procedures Online, vol. 11, No. 1, 2009, pp. 32-51 (Year: 2009).*

(Continued)

*Primary Examiner* — Jon Chang
(74) *Attorney, Agent, or Firm* — Chip Law Group

(57) ABSTRACT

The present technology relates to an information processing device and an information processing method for enabling continuous measurement of information in a body. The information processing device includes a light emitting unit that emits light of a predetermined wavelength, an imaging unit that captures reflected light from an object, an analysis unit that analyzes an image captured by the imaging unit, a storage unit that stores an analysis result analyzed by the analysis unit, a communication unit that transmits the analysis result stored in the storage unit to another device, and a battery unit that generates and stores power to supply electric power to each unit, and the information processing device is embedded in a body to operate. The light emitting (Continued)

unit emits beams of light of different wavelengths. For example, the light emitting unit emits infrared light and red light, and the analysis unit measures oxygen saturation in blood using a ratio of reflected light of the infrared light to reflected light of the red light. The present technology can be applied to an information processing device that is embedded in a body and acquires information related to physical condition.

10 Claims, 6 Drawing Sheets

(51) Int. Cl.
*A61B 5/1455* (2006.01)
*A61B 5/022* (2006.01)
(52) U.S. Cl.
CPC .......... *A61B 5/14551* (2013.01); *H01M 8/16* (2013.01); *H01M 2250/30* (2013.01); *Y02E 60/527* (2013.01)

(56) References Cited

U.S. PATENT DOCUMENTS

| | | | | |
|---|---|---|---|---|
| 6,588,901 | B1 * | 7/2003 | Grinvald | A61B 3/1241 |
| | | | | 351/206 |
| 2008/0044721 | A1 * | 2/2008 | Heller | C12Q 1/26 |
| | | | | 429/2 |
| 2010/0185055 | A1 | 7/2010 | Robertson et al. | |
| 2013/0289372 | A1 * | 10/2013 | Imran | A61B 5/1459 |
| | | | | 600/339 |
| 2015/0051465 | A1 | 2/2015 | Robertson et al. | |

FOREIGN PATENT DOCUMENTS

| | | |
|---|---|---|
| DE | 69602365 T2 | 11/1999 |
| DE | 69527916 T2 | 4/2003 |
| EP | 0714628 A1 | 6/1996 |
| ES | 2132924 T3 | 8/1999 |
| JP | 06-121785 A | 5/1994 |
| JP | 08-206101 A | 8/1996 |
| JP | 11-507556 A | 7/1997 |
| JP | 11-507556 A | 7/1999 |
| JP | 2005-310613 A | 11/2005 |
| JP | 2010-139510 A | 6/2010 |
| JP | 2010-524512 A | 7/2010 |
| JP | 2014-054558 A | 3/2014 |
| JP | 5524626 B2 | 6/2014 |
| JP | 2015-107342 A | 6/2015 |
| SG | 178740 A1 | 3/2012 |
| WO | 96/41290 A1 | 12/1996 |
| WO | 2008/095183 A2 | 8/2008 |

OTHER PUBLICATIONS

Theodor et al. "Implantable Pulse Oximetry on Subcutaneous Tissue." 36th Annual International Conference of the IEEE Engineering in Medicine and Biology Society, Aug. 26, 2014, pp. 2089-2092 (Year: 2014).*

Reichelt et al. "Development of an Implantable Pulse Oximeter." IEEE Transactions on Biomedical Engineering, vol. 55, No. 2, Feb. 2008, pp. 581-588 (Year: 2008).* ePhotozine article, Complete Guide to Image Sensor Pixel Size, at https://www.ephotozine.com/article/complete-guide-to-image-sensor-pixel-size-29652 (retrieved Jun. 10, 2019) (Year: 2019).*

Wikipedia article, Red Blood Cell at https://en.wikipedia.org/wiki/Red_blood_cell#Structure, (retrieved Jun. 10, 2019) (Year: 2019).*

International Search Report and Written Opinion of PCT Application No. PCT/JP2016/071565, dated Sep. 6, 2016, 11 pages of ISRWO.

* cited by examiner

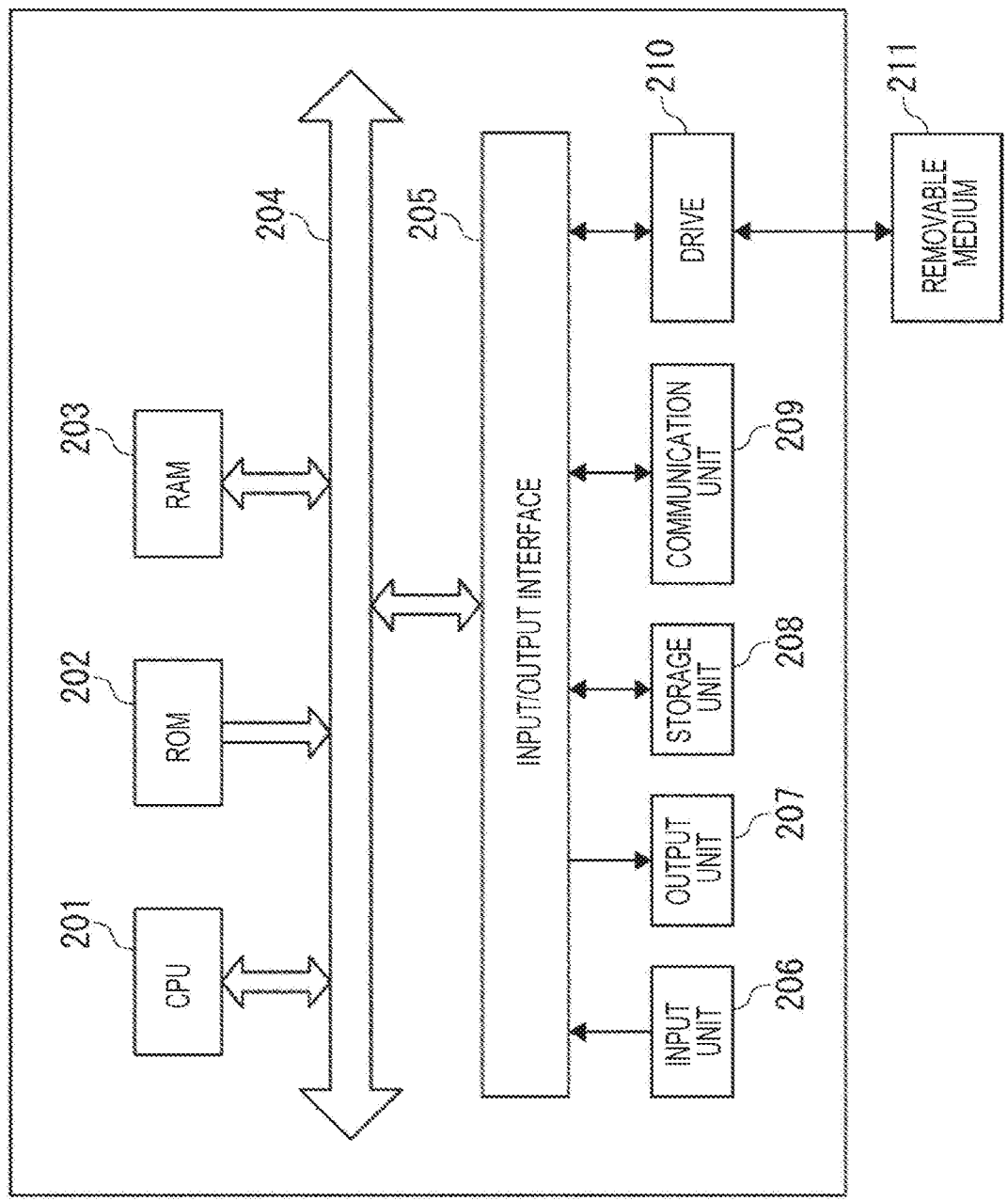

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2016/071565 filed on Jul. 22, 2016, which claims priority benefit of Japanese Patent Application No. JP 2015-156080 filed in the Japan Patent Office on Aug. 6, 2015. Each of the above-referenced applications is hereby incorporated herein by reference in its entirety.

TECHNICAL FIELD

The present technology relates to an information processing device, an information processing method, and a program. More specifically, the present technology relates to an information processing device, an information processing method, and a program for obtaining predetermined information from the inside of a body and processing the information.

BACKGROUND ART

Users' interest in health has been increasing, and the demand for maintaining health has also been increasing. Blood pressure measuring instruments and the like that can measure blood pressure in homes and the like have also been spreading. In addition, Patent Document 1 describes a noninvasive constituent concentration measuring device and a method for controlling the constituent concentration measuring device.

CITATION LIST

Patent Document

Patent Document 1: Japanese Patent Application Laid-Open No. 2010-139510

SUMMARY OF THE INVENTION

Problems to be Solved by the Invention

The conventional blood pressure measuring instruments, the constituent concentration measuring device proposed in Patent Document 1, and the like can measure only at a place where the device is located. For example, even if a user desires to measure when a change in physical condition is felt, the user cannot measure without a device. In addition, it is difficult to measure all the time with such a device, and it is difficult to detect changes in physical condition.

The present technology has been made in view of such a situation in order to enable detection of changes in physical condition.

Solutions to Problems

An information processing device according to an aspect of the present technology includes: a light emitting unit that emits light of a predetermined wavelength; an imaging unit that captures reflected light from an object; an analysis unit that analyzes an image captured by the imaging unit; a storage unit that stores an analysis result analyzed by the analysis unit; a communication unit that transmits the analysis result stored in the storage unit to another device; and a battery unit that generates and stores power to supply electric power to each unit, and the information processing device is embedded in a body to operate.

The light emitting unit can emit beams of light of different wavelengths.

The light emitting unit can emit infrared light and red light, and the analysis unit can measure oxygen saturation in blood using a ratio of reflected light of the infrared light to reflected light of the red light.

One side of one pixel constituting the imaging unit can have a smaller size than an erythrocyte.

The imaging unit can capture the erythrocyte, and the analysis unit can calculate a moving distance of the erythrocyte captured, and measure a velocity of blood flow.

Light emission by the light emitting unit and communication by the communication unit can be performed in a time division manner.

The battery unit can include a bio-battery.

The other device can be a mobile terminal, and issue an alert in a case where the analysis result indicates an abnormality in the body.

An information processing method according to an aspect of the present technology is an information processing device including: a light emitting unit that emits light of a predetermined wavelength; an imaging unit that captures reflected light from an object; and a battery unit that generates and stores power to supply electric power to each unit, the information processing device is embedded in a body to operate, and the information processing method includes the steps of: analyzing an image captured by the imaging unit; and transmitting an analysis result analyzed to another device.

A program according to an aspect of the present technology causes a computer that controls an information processing device to execute a process, the information processing device includes: a light emitting unit that emits light of a predetermined wavelength; an imaging unit that captures reflected light from an object; and a battery unit that generates and stores power to supply electric power to each unit, the information processing device is embedded in a body to operate, and the process includes the steps of: analyzing an image captured by the imaging unit; and transmitting an analysis result analyzed to another device.

In an information processing device, an information processing method, and a program according to an aspect of the present technology, light of a predetermined wavelength is emitted, reflected light from an object is captured, a captured image is analyzed, an analysis result analyzed is stored, the analysis result stored is transmitted to another device, and a battery unit that generates and stores power to supply electric power to each unit is provided.

Effects of the Invention

According to an aspect of the present technology, changes in physical condition can be detected.

Note that the effects described herein are not necessarily limited, and any of the effects described in the present disclosure may be obtained.

BRIEF DESCRIPTION OF DRAWINGS

FIG. 8 is a diagram for explaining a recording medium.

MODE FOR CARRYING OUT THE INVENTION

Hereinafter, a mode for carrying out the present technology (hereinafter referred to as an "embodiment") will be described. Note that the description will be provided in the following order:

1. Configuration of System
2. Configuration of Information Processing Device
3. Operation of Information Processing Device
4. Regarding Recording Medium <Configuration of System>

Figure 1:
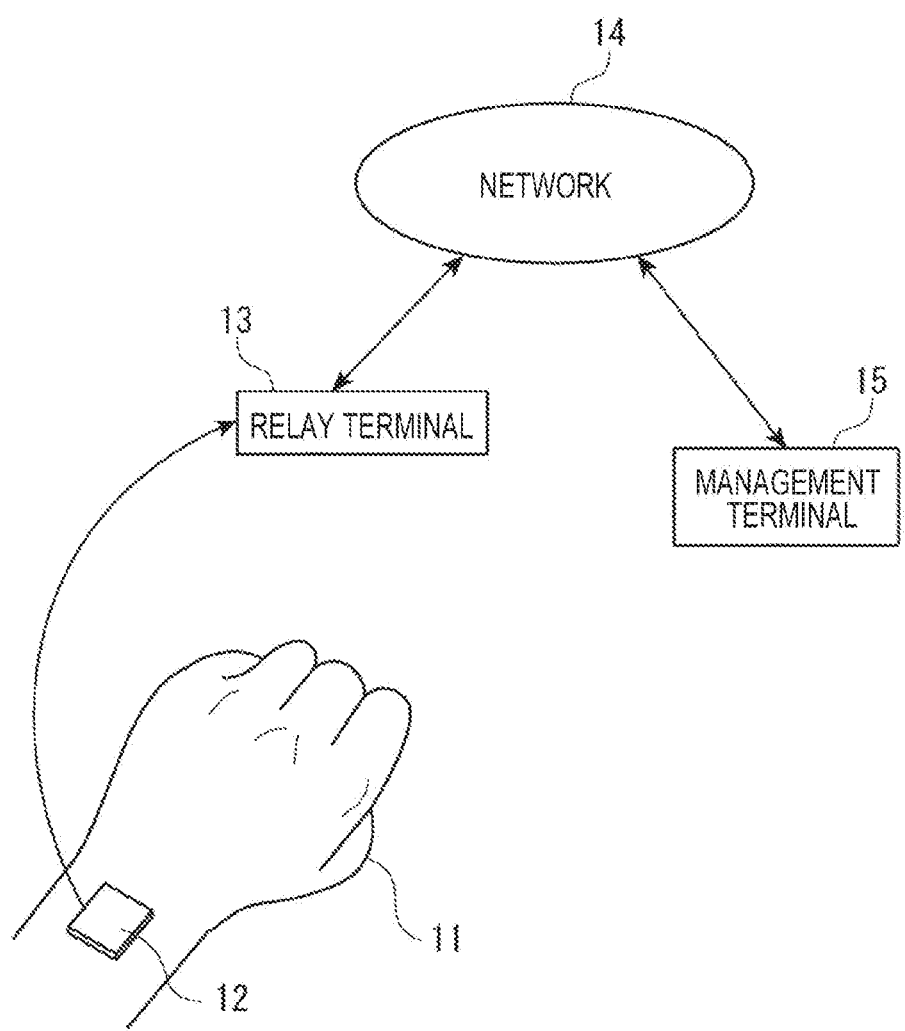
FIG. 1 is a diagram illustrating a configuration of an embodiment of an information processing system to which the present technology is applied.

FIG. 1 is a diagram illustrating a configuration of an embodiment of an information processing system to which the present technology is applied. The present technology can be applied to a system which is embedded in a predetermined position inside a human body, measures predetermined information, e.g., blood pressure and the like, and outputs values measured at predetermined intervals to a device outside the body.

The information processing system includes an information processing device 12 embedded, for example, in an arm 11 of a human, a relay terminal 13, a network 14, and a management terminal 15. The information processing device 12 has a configuration to be described later with reference to FIG. 2, and collects information such as blood flow and oxygen concentration. The relay terminal 13 is a terminal that can be configured by a mobile terminal such as a mobile phone (smartphone), for example, and is capable of communicating with the information processing device 12.

The information processing device 12 transmits the collected information to the relay terminal 13 at predetermined intervals. The relay terminal 13 may be configured to store the received information, or may be configured to supply the received information to the management terminal 15 via the network 14.

Specifically, the information collected by the information processing device 12 can be viewed, analyzed, and managed at the relay terminal 13, or can be viewed, analyzed, and managed at the management terminal 15. Alternatively, the information collected by the information processing device 12 can be viewed, analyzed, and managed at both the relay terminal 13 and the management terminal 15.

The management terminal 15 can be configured by, for example, a personal computer. Further, the management terminal 15 can be, for example, a terminal installed in a hospital, and it is also possible to construct a mechanism that makes the hospital staff take action in the event that the information collected by the information processing device 12 indicates that an abnormality has occurred in the person of the arm 11.

<Configuration of Information Processing Device>

Figure 2:
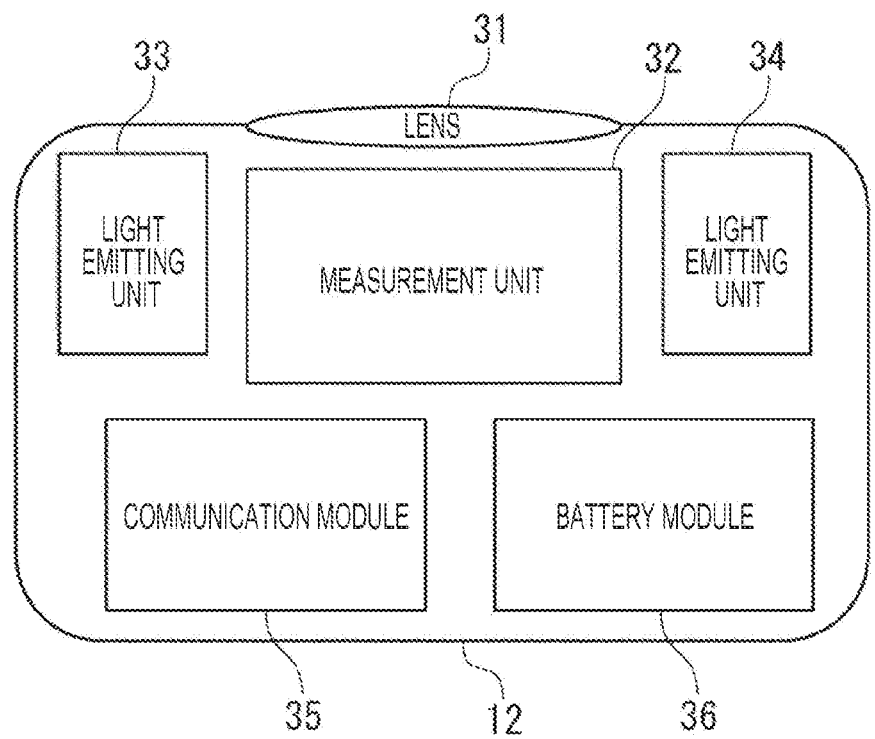
FIG. 2 is a diagram illustrating a configuration of an information processing device.

FIG. 2 is a diagram illustrating a configuration of the information processing device 12. The information processing device 12 includes a lens 31, a measurement unit 32, a light emitting unit 33, a light emitting unit 34, a communication module 35, and a battery module 36.

The information processing device 12 is configured to measure, for example, the amount of oxygen in a result in such a manner that light emitted by the light emitting units 33 and 34 reaches an object, e.g., hemoglobin flowing through a blood vessel, and the measurement unit 32 observes (captures) the reflected wave reflected by the object.

The communication module 35 is a module that communicates with the relay terminal 13. The battery module 36 is a module having the function of generating and storing power in order to supply electric power to each part in the information processing device 12.

Figure 3:
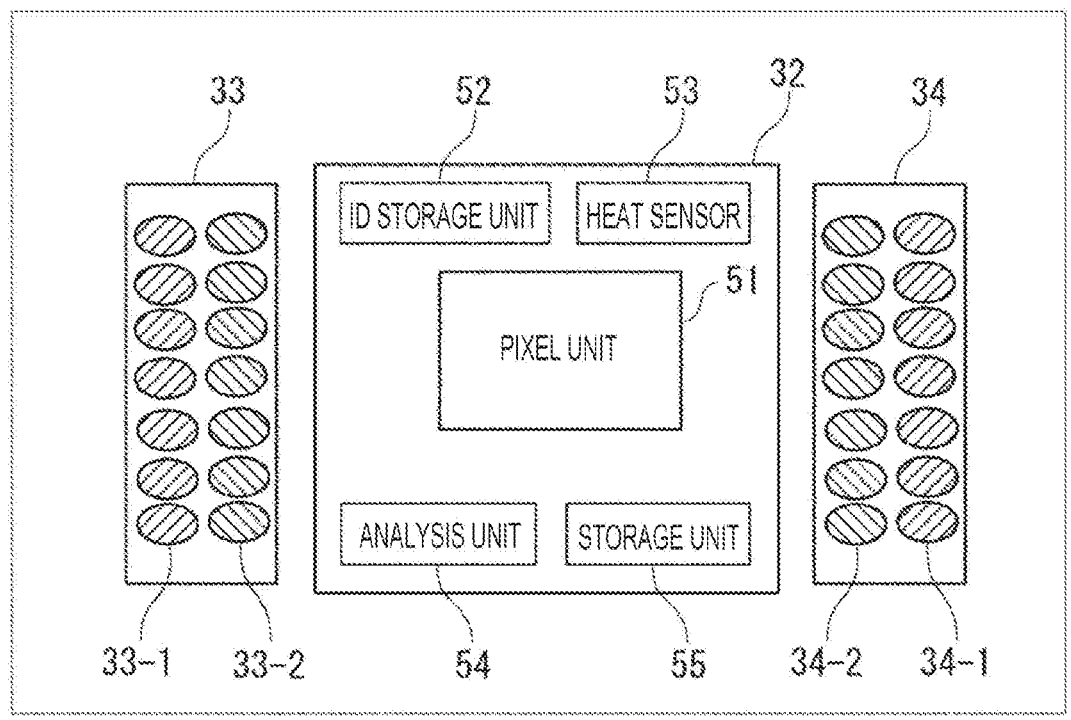
FIG. 3 is a diagram illustrating a configuration of a measurement unit.

FIG. 3 is a diagram illustrating configurations of the measurement unit 32 and the light emitting units 33 and 34. The measurement unit 32 is configured to include a pixel unit 51, an ID storage unit 52, a heat sensor 53, an analysis unit 54, and a storage unit 55.

The light emitting unit 33 includes a light emitting unit 33-1 and a light emitting unit 33-2. The light emitting unit 33-1 and the light emitting unit 33-2 can be light emitting units that emit beams of light of different wavelengths. For example, the light emitted by the light emitting unit 33-1 can be red light, and the light emitted by the light emitting unit 33-2 can be infrared light.

Similarly, the light emitting unit 34 also includes a light emitting unit 34-1 and a light emitting unit 34-2. The light emitting unit 34-1 and the light emitting unit 34-2 can be light emitting units that emit beams of light of different wavelengths. For example, the light emitting unit 34-1 can be a light emitting unit that emits red light, and the light emitting unit 34-2 can be a light emitting unit that emits infrared light.

The light emitting unit 33-1 and the light emitting unit 34-1 may be configured as light emitting units that emit beams of light of the same wavelength, or may be configured as light emitting units that emit beams of light of different wavelengths. Similarly, the light emitting unit 33-2 and the light emitting unit 34-2 may be configured as light emitting units that emit beams of light of the same wavelength, or may be configured as light emitting units that emit beams of light of different wavelengths.

In the case of the configuration for emitting similar beams of light, the information processing device 12 is configured to collect predetermined information using beams of light of two kinds of wavelengths. In the case of the configuration for emitting different beams of light, the information processing device 12 is configured to collect predetermined information using beams of light of four kinds of wavelengths.

Here, description will be continued on the assumption that the information processing device 12 is configured to collect predetermined information using beams of light of two kinds of wavelengths. However, light of a wavelength suitable for information to be collected can be used, or a light emitting unit that emits beams of light of one or more wavelengths may be provided.

In the following description, it is assumed that the light emitting unit 33 and the light emitting unit 34 have similar configurations, and the information processing device 12 collects predetermined information using beams of light of two kinds of wavelengths. In addition, the light emitting unit 33 will be described as an example unless the light emitting units need to be particularly distinguished form each other. However, when the light emitting unit 33 emits light, the light emitting unit 34 also emits light.

Figure 4:
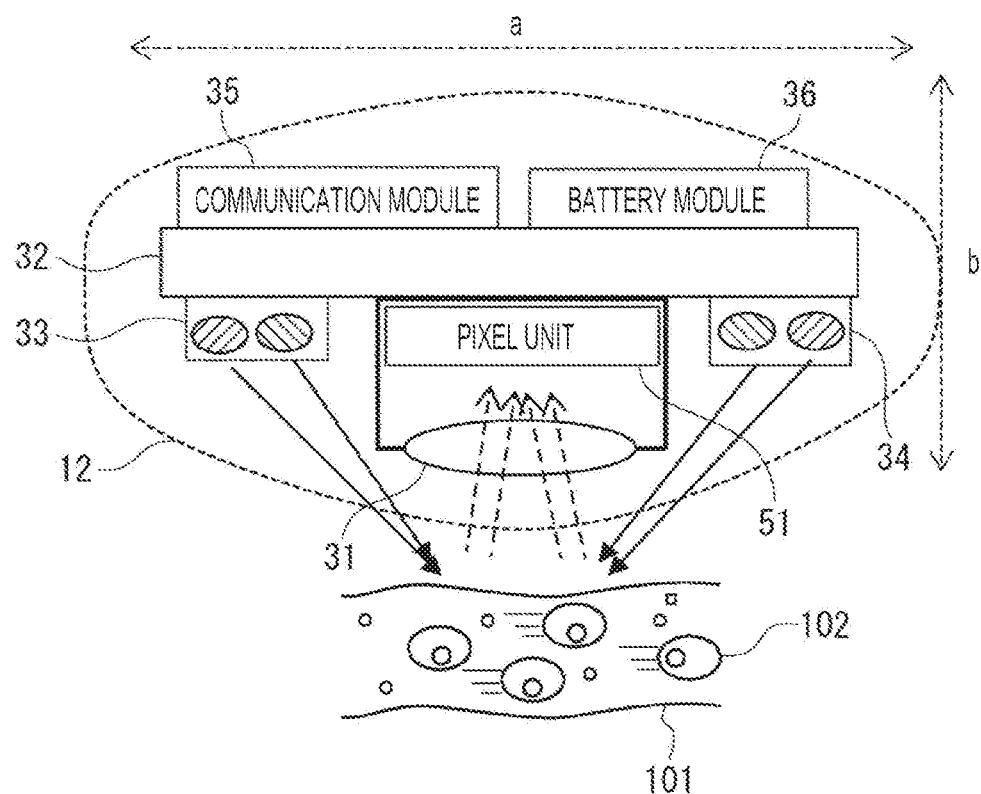
FIG. 4 is a diagram for explaining light emission and measurement.

As illustrated in FIG. 4, the information processing device 12 is embedded, for example, in a predetermined position of the arm 11 such that the lens 31 faces a blood vessel 101. Since the information processing device 12 is embedded in the body, the information processing device 12 has a small size of a×b or less as illustrated in FIG. 4. For example, a is 2 mm and b is 1.5 mm.

The light emitted from the light emitting unit 33 of the information processing device 12 reaches, for example, an erythrocyte 102 of the blood vessel 101 to be reflected and enter the pixel unit 51 via the lens 31. The pixel unit 51 includes, for example, a complementary MOS (CMOS) image sensor. Further, the pixel unit 51 has a configuration in which a plurality of pixels, for example, 100×100 pixels, are arranged in a two-dimensional array.

Red light and infrared light are used as the light emitting unit 33, the reflected light from the erythrocyte 102 due to the radiation of red light is captured by the pixel unit 51, the reflected light from the erythrocyte 102 due to the radiation of infrared light is captured by the pixel unit 51, and the analysis unit 54 compares and analyzes the respective images. Consequently, for example, oxygen saturation in the blood is detected, and the detected value is stored in the storage unit 55.

Figure 5:
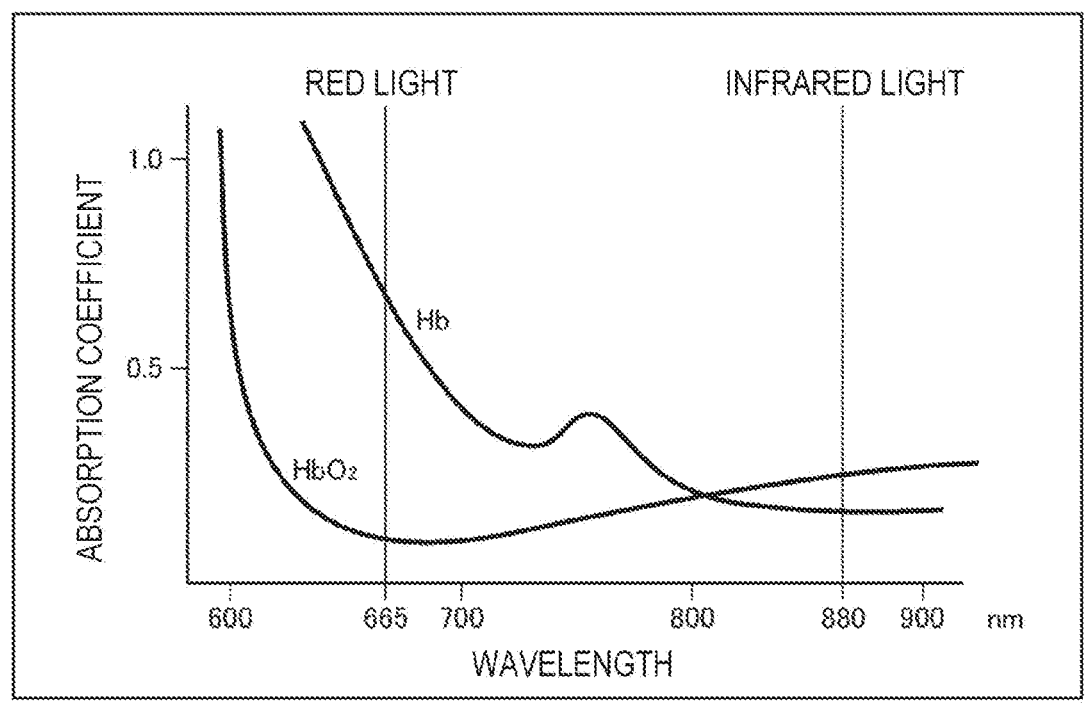
FIG. 5 is a diagram for explaining the absorption coefficient of hemoglobin.

FIG. 5 illustrates an absorbance curve indicating which light is much absorbed by hemoglobin combined with oxygen (HbO2) and by hemoglobin that has released oxygen (Hb). The horizontal axis represents the wavelength of light, and the vertical axis represents the absorption coefficient. The two graphs illustrated in FIG. 5 indicate which wavelengths are well absorbed and which wavelengths are not absorbed so much by HbO2 and Hb. As the line of the graph goes downward, it means that light of that wavelength is less absorbed, in other words, light of that wavelength passes more easily.

Hemoglobin combined with oxygen (HbO2) is red because it does not absorb so much but transmits only the red color. This therefore indicates that the absorbance of red color is low. On the other hand, hemoglobin that has released oxygen (Hb) is relatively dark. This is because it absorbs light well.

In a case where red light is applied to the blood, if hemoglobin is combined with more oxygen, more light passes through the blood vessel 101, and a smaller amount of light is reflected by the hemoglobin and received by the pixel unit 51. Almost the same amount of infrared light passes through the blood no matter whether hemoglobin is combined with oxygen or not.

If HbO2 increases and Hb decreases, the amount of red light (R) captured by the pixel unit 51 decreases and the amount of infrared light (IR) does not change so much. If HbO2 decreases and Hb increases, the amount of red light (R) captured by the pixel unit 51 increases and the amount of infrared light (IR) does not change so much.

Therefore, if the ratio (R/IR) of red light to infrared light captured by the pixel unit 51 is analyzed, the ratio of HbO2 to Hb, namely, oxygen saturation, can be analyzed. In this manner, the information processing device 12 measures the oxygen saturation in the blood.

Figure 6:
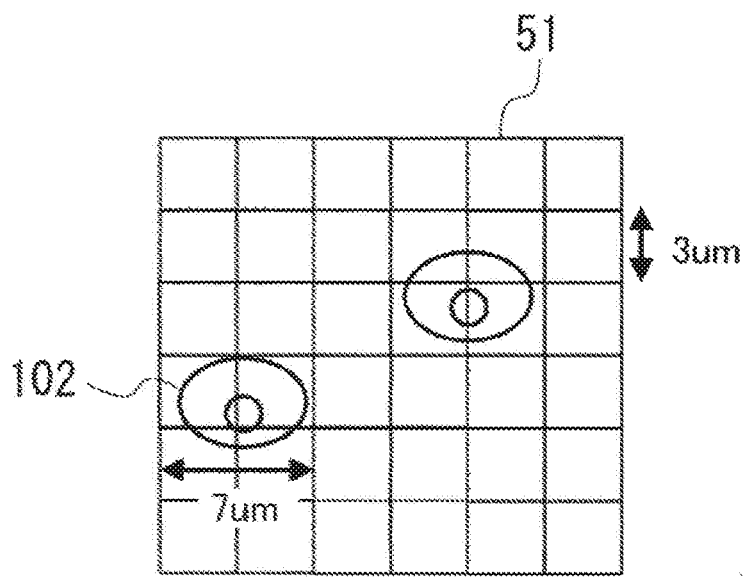
FIG. 6 is a diagram for explaining the size of a pixel.

Alternatively, the blood flow velocity may be detected by the information processing device 12. As illustrated in FIG. 6, the size of each pixel of the pixel unit 51 is set such that one side has a length of 3 um or less. The size of the erythrocyte 102 is about 7 um. In a case where the size of the pixel of the pixel unit 51 is 3 um, it is less than half the size of the erythrocyte 102 (7 um).

In a case where the size of one pixel is 3 um and the pixel unit 51 is configured with 100×100 pixels, the length of one side of the pixel unit 51 is 300 um. The blood flow velocity is, for example, about 300 um/s in the case of a capillary blood vessel. For example, the blood flow velocity can be measured by capturing about 10 frames per second. For example, the moving distance of the erythrocyte 102 is calculated from the coordinates of the erythrocyte 102 captured in the first frame and the coordinates of the erythrocyte 102 captured in the second frame, whereby the blood flow velocity can be calculated.

As illustrated in FIG. 3, the information processing device 12 may have a configuration in which the heat sensor 53 is mounted. In a case where the heat sensor 53 is mounted, the body temperature can be measured.

As described above, the information processing device 12 can measure the oxygen saturation in the blood, blood flow velocity, body temperature, and the like. In the described example, the oxygen saturation is measured using red light and infrared light, but the oxygen saturation can be measured using light of another wavelength.

Further, ultraviolet light, visible light, or the like may be used. A measuring object can be measured by emitting, capturing, and analyzing light suitable for the measuring object. The above example is merely an example and not a description that limits the scope of application of the present technology.

The information processing device 12 can also be configured to be able to obtain information of pulse rate and blood pressure by using the flow velocity of erythrocytes as a measuring object. For example, the analysis unit 54 of the measurement unit 32 measures the flow velocity of erythrocytes, stores it in the storage unit 55, and transmits it to the relay terminal 13 at a predetermined timing. The flow velocity of erythrocytes may further be transmitted from the relay terminal 13 to the management terminal 15. In this description, it is assumed that the relay terminal 13 executes the following process, but the management terminal 15 can be configured to perform the process.

The relay terminal 13 calculates the pulse rate and blood pressure from the received flow velocity of erythrocytes. Information of pulse rate and blood pressure may be generated by the analysis unit 54, stored in the storage unit 55, and transmitted to the relay terminal 13. By accumulating and analyzing the information of pulse rate and blood pressure in the relay terminal 13 and the management terminal 15, symptoms of heart disease and the like can be detected, for example.

Furthermore, it can be applied to living improvement, medicine administration, and the like. For example, when it can be determined that the blood pressure is rising, an alert can be given to a user (person to be measured, patient, or the like.) or an instruction to take medicine can be given (message or the like is displayed on the relay terminal 13).

In addition, the information processing device 12 can also be configured to be able to obtain information of thickness of blood by using the number of erythrocytes per unit as a measuring object. By accumulating and analyzing the information of thickness of blood in the relay terminal 13 and the management terminal 15, symptoms of cerebral infarction, heatstroke, and the like can be detected, for example.

Furthermore, it can be applied to a hydration alarm and the like. For example, when it can be determined that the thickness of blood is rising, an alert can be given to a user or an instruction to drink fluids can be given (message or the like is displayed on the relay terminal 13).

In addition, the information processing device 12 can also be configured to be able to obtain information of oxygen concentration in blood by using the color shade of hemoglobin as a measuring object as described above. By accumulating and analyzing the information of oxygen concentration in blood in the relay terminal 13 and the management terminal 15, symptoms of bronchial disease, apnea syndrome, and the like can be detected, for example. Furthermore, it can be applied to shortening the apnea time by sounding an alarm during apnea, and the like.

In addition, the information processing device 12 can also be configured to be able to obtain information of sugar content in blood by using the spectrum due to near infrared spectroscopy as a measuring object. By accumulating and analyzing the information of sugar content in blood in the relay terminal 13 and the management terminal 15, symptoms of diabetes and the like can be detected, for example. Furthermore, it can be applied to an improvement in diet, an insulin administration alarm, and the like.

<Operation of Information Processing Device>

Figure 7:
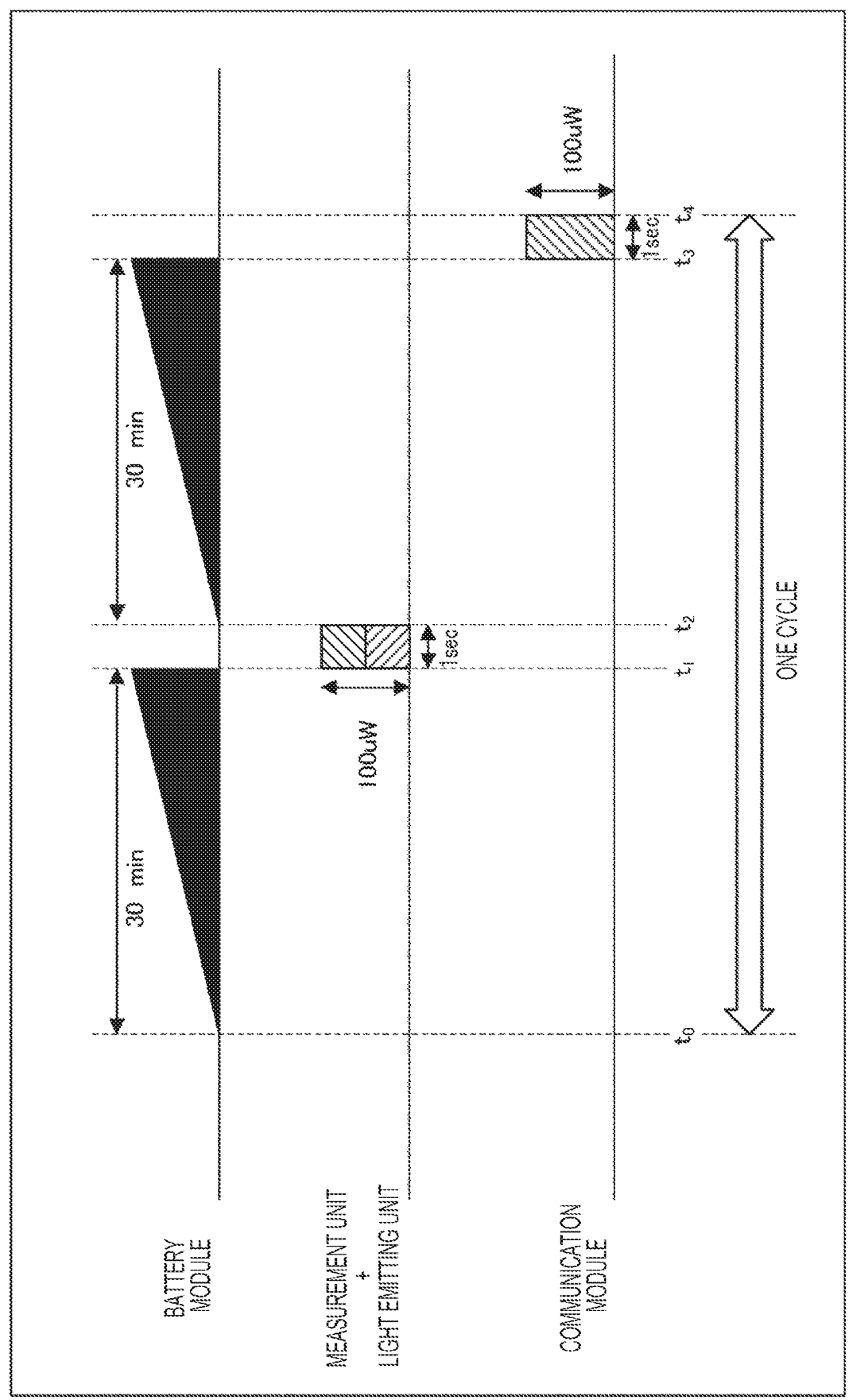
FIG. 7 is a diagram for explaining the operation of the information processing device.

The operation of the information processing device 12 will be described with reference to FIG. 7. In the described example, assuming that one cycle is one hour, one measurement and one transmission (communication) are performed in one cycle. Note that one cycle is assumed to be, but not limited to, one hour, and may be 30 minutes, two hours, or the like.

The battery module 36 charges for 30 minutes (30 min) from time t0 to time t1. Since the battery module 36 is embedded in the body and difficult to replace, the battery module 36 has the function of generating and accumulating power by itself.

For example, the battery module 36 may be configured to include a battery called a bio-battery or the like. The bio-battery is exemplified by a battery that generates power with glucose, for example. The bio-battery that generates power with glucose is structured such that a separator is sandwiched between an electrode (negative electrode) at which enzymes that decompose glucose and electron mediators are immobilized and an electrode (positive electrode) at which enzymes for the reduction of oxygen and electron mediators are immobilized.

On the negative electrode side, an aqueous solution of glucose is taken from the outside, and electrons and hydrogen ions are extracted when the glucose is oxidatively decomposed by enzymes. In addition, the hydrogen ions move from the negative electrode side to the positive electrode side via the separator. On the positive electrode side, oxygen in the air is taken, and water is generated by a reduction reaction with electrons and hydrogen ions. Through this series of electrochemical reactions, electric energy is extracted as electrons move through an external circuit.

Such a bio-battery with the use of glucose may be included in the battery module 36. Further, for example, an element that performs power generation by body temperature (heat) or performs power generation using vibration may be included in the battery module 36. Alternatively, using a non-contact power transmission technology, for example, the user may periodically bring the relay terminal 13 closer to the information processing device 12, and charging may be performed at that time.

An element having the function of storing power such as a capacitor is also included in the battery module 36, and the generated electric power is stored in a power storage unit. Such charging is first performed between time t0 and time t1. For example, the capacitor having a capacitance of 100 μF is charged.

At time t1, the light emitting unit 33 and the light emitting unit 34 emit light, and the measurement unit 32 captures the reflected light of the emitted light. Further, the measurement unit 32 acquires predetermined information by analyzing the measurement result. At this time, the light emission in the light emitting units 33 and 34 and the measurement in the measurement unit 32 are performed using the electric power stored in the battery module 36. Further, in this configuration, the light emission and measurement are ended within a relatively short time, e.g., one second (1 sec).

The light emission and measurement consume, for example, electric power of 100 uW. Out of the electric power of 100 uW, electric power of 50 uW is used for the light emitting operation of the light emitting units 33 and 34, and electric power of 50 uW is used for the measurement operation of the measurement unit 32.

Once the light emission and measurement are ended at time t2, the measurement result is stored in the storage unit 55 (FIG. 3) of the measurement unit 32. Further, charging in the battery module 36 is started at time t2. The battery module 36 is charged from time t2 to time t3.

At time t3, communication by the communication module 35 is executed. The communication consumes, for example, electric power of 100 uW. The communication by the communication module 35 is performed in such a manner that the information stored in the storage unit 55 in the measurement unit 32 is read and transmitted to the relay terminal 13 in association with the ID stored in the ID storage unit 52.

In this configuration, the communication is ended within a relatively short time, e.g., one second (1 sec). For example, the communication can be performed using Bluetooth (registered trademark).

Note that if there is no measured information (if there is no information stored in the storage unit 55), only the ID may be transmitted.

As described above, the measurement operation and the communication operation are processed in a time division manner, whereby the electric power related to the measurement operation and the communication operation can be dispersed. If the measurement operation and the communication operation are performed at the same time (continuously), in the above example, electric power of 200 uw is required, and the capacitance for charging the battery module 36 needs the ability to enable the acquisition of electric power of 200 uw.

However, as described above, the measurement operation and the communication operation are processed in a time division manner, whereby the electric power related to the measurement operation and the communication operation can be dispersed, and the capacitance for charging the battery module 36 only needs the ability to enable the acquisition of electric power of 100 uw.

In consideration of embedding the information processing device 12 in the body, there is a possibility that it is difficult to increase the power generation capability of the battery module 36 or increase the power storage capacitance. Therefore, in order to cause the information processing device 12 to operate despite the low power generation capability of the battery module 36 or small power storage capacitance, it is effective to process the measurement operation and the communication operation in a time division manner.

As described above, according to the present technology, it is possible to acquire information related to physical condition by the information processing device 12 and periodically supply the information to the relay terminal 13 and the management terminal 15. For example, in the case of the conventional blood pressure measuring instrument, measurement can be performed only at a place where the measuring instrument is located. However, according to the present technology, it is possible to perform measurement irrespective of the location of the measuring instrument. Therefore, measurement can be performed more than once a day, which enables continuous measurement.

In the above example, measurement can be performed about once every hour. Therefore, it is possible to frequently measure and record changes in physical condition within a day. Moreover, such measurement does not have to be consciously performed by the user, for example, by wearing a blood pressure measuring instrument and measuring blood pressure, but can be unconsciously performed by the user (patient) (automatically for the user). This makes it possible to reduce the psychological burden on the user.

In addition, since it is possible to monitor the physical condition with the relay terminal 13 and the management terminal 15, as described above, an alert that prompts the user to receive hydration or an alert that prompts the user to take medicine can be issued according to changes in physical condition. In addition, if the management terminal 15 manages and analyzes the information obtained by the information processing device 12, more precise analysis can be performed, which can be applied to early detection of diseases or the like.

Note that a plurality of information processing devices 12 may be embedded in one human body instead of the only one information processing device 12. In addition, different types of information can be acquired by the information processing devices 12 embedded in different places, and the physical condition of the individual can be monitored on the basis of a plurality of types of information.

<Regarding Recording Medium>

The above-mentioned sequence of processes can be executed by hardware, and can also be executed by software. In a case where the sequence of processes is executed by the software, a program constituting the software is installed on a computer. As used herein, the computer includes a computer incorporated in dedicated hardware or, for example, a general personal computer or the like that can install various programs to execute various functions.

FIG. 8 is a block diagram illustrating an exemplary configuration of the hardware of the computer that executes the above-mentioned sequence of processes by means of the program. In the computer, a central processing unit (CPU) 201, a read only memory (ROM) 202, and a random access memory (RAM) 203 are coupled to one another by a bus 204. An input/output interface 205 is further connected to the bus 204. An input unit 206, an output unit 207, a storage unit 208, a communication unit 209, and a drive 210 are connected to the input/output interface 205.

The input unit 206 includes a keyboard, a mouse, a microphone, and the like. The output unit 207 includes a display, a speaker, and the like. The storage unit 208 includes a hard disc, a non-volatile memory, and the like. The communication unit 209 includes a network interface or the like. The drive 210 drives a removable medium 211 such as a magnetic disc, an optical disc, a magneto-optical disc, or a semiconductor memory.

In the computer configured as mentioned above, the CPU 201 loads, for example, the program stored in the storage unit 208 on the RAM 203 via the input/output interface 205 and the bus 204, and executes the program, whereby the above-mentioned sequence of processes is performed.

The program that is executed by the computer (CPU 201) can be recorded in the removable medium 211 serving as, for example, a package medium or the like, and provided. Alternatively, the program can be provided through a wired or wireless transmission medium such as a local area network, the Internet, and digital satellite broadcasting.

In the computer, the program can be installed on the storage unit 208 via the input/output interface 205 when the removable medium 211 is mounted in the drive 210. Alternatively, the program can be received at the communication unit 209 via a wired or wireless transmission medium, and installed on the storage unit 208. Additionally, the program can be installed in advance on the ROM 202 or the storage unit 208.

Note that the program that is executed by the computer may be such a program that the processes are performed in time series in the order described in the present description, or may be such a program that the processes are performed parallelly or at a necessary timing, i.e., when a call is performed, for example.

In addition, the system in the present description represents an entire device including a plurality of devices.

Note that the effects described in the present description are only examples, and are not limited to these effects. Other effects may also be obtained.

Note that the embodiment of the present technology is not limited to the above-mentioned embodiment, and can be variously changed in a range not departing from the gist of the present technology.

Note that the present technology can also be configured as follows.

(1)

An information processing device including:

a light emitting unit that emits light of a predetermined wavelength;

an imaging unit that captures reflected light from an object;

an analysis unit that analyzes an image captured by the imaging unit;

a storage unit that stores an analysis result analyzed by the analysis unit;

a communication unit that transmits the analysis result stored in the storage unit to another device; and a battery unit that generates and stores power to supply electric power to each unit, in which the information processing device is embedded in a body to operate.

(2)

The information processing device according to (1), in which the light emitting unit emits beams of light of different wavelengths.

(3)

The information processing device according to (1) or (2), in which the light emitting unit emits infrared light and red light, and the analysis unit measures oxygen saturation in blood using a ratio of reflected light of the infrared light to reflected light of the red light.

(4)

The information processing device according to any of (1) to (3), in which one side of one pixel constituting the imaging unit has a smaller size than an erythrocyte.

(5)

The information processing device according to any of (1) to (4), in which the imaging unit captures the erythrocyte, and the analysis unit calculates a moving distance of the erythrocyte captured, and measures a velocity of blood flow.

(6)

The information processing device according to any of (1) to (5), in which light emission by the light emitting unit and communication by the communication unit are performed in a time division manner.

(7)

The information processing device according to any of (1) to (6), in which the battery unit includes a bio-battery.

(8)

The information processing device according to any of (1) to (7), in which the other device is a mobile terminal, and issues an alert in a case where the analysis result indicates an abnormality in the body.

(9)

An information processing method that is an information processing device including:

a light emitting unit that emits light of a predetermined wavelength;

an imaging unit that captures reflected light from an object; and a battery unit that generates and stores power to supply electric power to each unit, in which the information processing device is embedded in a body to operate, and the information processing method includes the steps of:

analyzing an image captured by the imaging unit; and transmitting an analysis result analyzed to another device.

(10)

A computer-readable program for causing a computer that controls an information processing device to execute a process, the information processing device including:

a light emitting unit that emits light of a predetermined wavelength;

an imaging unit that captures reflected light from an object; and a battery unit that generates and stores power to supply electric power to each unit, in which the information processing device is embedded in a body to operate, and the process includes the steps of:

analyzing an image captured by the imaging unit; and transmitting an analysis result analyzed to another device.

REFERENCE SIGNS LIST

12 Information processing device
13 Relay terminal
15 Management terminal
31 Lens
32 Measurement unit
33, 34 Light emitting unit
35 Communication module
36 Battery module
51 Pixel unit
52 ID storage unit
53 Heat sensor
54 Analysis unit
55 Storage unit

The invention claimed is:

1. An information processing device, comprising:
a light emitting unit configured to emit light of a specific wavelength;
an image sensor configured to capture an image based on reflected light from an object;
a central processing unit (CPU) configured to analyze the captured to output an analysis result;
a memory configured to store the analysis result, wherein the CPU is further configured to transmit the analysis result stored in the memory to a specific device; and
a battery unit configured to:
generate and store electric power;
supply, in a first time interval, a first amount of the electric power to each of the light emitting unit and the image sensor; and
supply, in a second time interval, a second amount of the electric power to the CPU, wherein
the second time interval is subsequent to the first time interval,
the second amount of the electric power is greater than the first amount of the electric power, and
the information processing device is embeddable in a body.

2. The information processing device according to claim 1, wherein the light emitting unit is further configured to emit beams of light of different wavelengths.

3. The information processing device according to claim 1, wherein
the light emitting unit is further configured to emit infrared light and red light, and
the CPU is further configured to measure oxygen saturation in blood based on a ratio of reflected light of the infrared light to reflected light of the red light.

4. The information processing device according to claim 1, wherein one side of one pixel constituting the imaging sensor has a size smaller than an erythrocyte.

5. The information processing device according to claim 1, wherein
the image sensor is further configured to capture an image of an erythrocyte, and
the CPU is further configured to:
calculate a moving distance of the erythrocyte based on the captured image of the erythrocyte; and
measure a velocity of blood flow based on the moving distance.

6. The information processing device according to claim 1, wherein the emission of the light and the transmission of the analysis result are in a time division manner.

7. The information processing device according to claim 1, wherein the battery unit includes a bio-battery.

8. The information processing device according to claim 1, wherein
the specific device is a mobile terminal, and
an alert is issued by the specific device based on the analysis result that indicates an abnormality in the body.

9. An information processing method, comprising:
in an information processing device that includes a light emitting unit, an image sensor, a central processing unit (CPU), a memory, and a battery unit:
emitting, by the light emitting unit, light of a specific wavelength;
capturing, by the image sensor, an image based on reflected light from an object;
analyzing, by the CPU, the captured image to output an analysis result;
storing the analysis result by the memory;
transmitting, by the CPU, the analysis result to a specific device;
generating and storing electric power by the battery unit;

supplying, by the battery unit, in a first time interval, a first amount of the electric power to each of the light emitting unit and the image sensor; and supplying, by the battery unit, in a second time interval, a second amount of the electric power to the CPU, wherein the second time interval is subsequent to the first time interval, the second amount of the electric power is greater than the first amount of the electric power, and the information processing device is embeddable in a body.

10. A non-transitory computer-readable medium having stored thereon computer-executable instructions that, when executed by a processor of an information processing device, cause the processor to execute operations, the operations comprising:

controlling a light emitting unit of the information processing device to emit light of a specific wavelength;

controlling an image sensor of the information processing device to capture an image based on reflected light from an object;

analyzing the captured image to output an analysis result;

storing the analysis result in a memory of the information processing device;

transmitting the analysis result to a specific device; and controlling a battery unit of the information processing device to:

generate and store electric power;

supply, in a first time interval, a first amount of the electric power to each of the light emitting unit and the image sensor; and supply, in a second time interval, a second amount of the electric power to the processor, wherein the second time interval is subsequent to the first time interval, the second amount of the electric power is greater than the first amount of the electric power, and the information processing device is embeddable in a body.

\* \* \* \* \*